US012605396B2

(12) United States Patent
Warrass et al.

(10) Patent No.: US 12,605,396 B2
(45) Date of Patent: Apr. 21, 2026

(54) METHODS OF TREATING MASTITIS WITH AN ORTHOSOMYCIN ANTIMICROBIAL COMPOUND

(71) Applicant: Intervet Inc., Madison, NJ (US)

(72) Inventors: Ralf Warrass, Alzey (DE); Joachim Ullrich, Stadecken-Elsheim (DE)

(73) Assignee: Intervet Inc., Rahway, NJ (US)

( * ) Notice: Subject to any disclaimer, the term of this patent is extended or adjusted under 35 U.S.C. 154(b) by 370 days.

(21) Appl. No.: 18/257,815

(22) PCT Filed: Dec. 23, 2021

(86) PCT No.: PCT/EP2021/087444

§ 371 (c)(1),
(2) Date: Jun. 15, 2023

(87) PCT Pub. No.: WO2022/136622

PCT Pub. Date: Jun. 30, 2022

(65) Prior Publication Data

US 2024/0058366 A1 Feb. 22, 2024

(30) Foreign Application Priority Data

Dec. 24, 2020 (EP) .................................... 20217194

(51) Int. Cl.

| | |
|---|---|
| ***A61K 31/7048*** | (2006.01) |
| ***A61K 9/00*** | (2006.01) |
| ***A61K 35/06*** | (2006.01) |
| ***A61K 45/06*** | (2006.01) |
| ***A61P 31/04*** | (2006.01) |

(52) U.S. Cl.

CPC ........ *A61K 31/7048* (2013.01); *A61K 9/0041* (2013.01); *A61K 45/06* (2013.01); *A61P 31/04* (2018.01)

(58) Field of Classification Search

None

See application file for complete search history.

(56) References Cited

U.S. PATENT DOCUMENTS

2015/0366797 A1* 12/2015 Page ....................... A61P 15/14
514/460

FOREIGN PATENT DOCUMENTS

| | | | | | |
|---|---|---|---|---|---|
| CN | 1843331 | A | | 10/2006 | |
| JP | 2010270016 | A | | 12/2010 | |
| JP | 2011050373 | A | | 3/2011 | |
| WO | 1998028011 | A1 | | 7/1998 | |
| WO | 2014001353 | A1 | | 1/2014 | |
| WO | 2014121343 | A1 | | 8/2014 | |
| WO | 2015114163 | A2 | | 8/2015 | |
| WO | 2017029271 | A1 | | 2/2017 | |
| WO | 2018195237 | A1 | | 10/2018 | |
| WO | WO-2019243345 | A1 | * | 12/2019 | ............. A23K 50/80 |

OTHER PUBLICATIONS

Kavault—avilamycin granule product sheet, Aug. 2015. (Year: 2015).*

Heike Kaspar, Results of the antimicrobial agent susceptibility study raised in a representative, cross-sectional monitoring study on a national basis, International Journal of Medical Microbiology, 296(S2), 69-79, 2006.

Wallmann, J'Urgen et al., Results of an interlaboratory test on antimicrobial susceptibility testing of bacteria from animals by broth microdilution, International Journal of Antimicrobial Agents, 27, 482-490, 2006.

CAS No. 109545-84-8, 2 pages.

Chu, M. et al., Isolation and Characterization of Novel Oligosaccharides Related to Ziracin, J. Nat. Prod., 2002, pp. 1588-1593, 65.

Nickerson, S. et al., Antibiotic Therapy in Mastitis Control for Lactating and Dry Cows Introduction, University of Georgia Extension, 2019, 1-11, N/A.

Ollis, David W. et al., The orthosomycin family of antibiotics-I, Tetrahedron, 1979, 105-127, 35(1).

Pyorala, S., Treatment of mastitis during lactation, Irish Veterinary Journal, 2009, 40-44, 62.

Wagman, G.H. et al., Fermentation and Isolation of Everninomicin, Antimicrobial Agents and Chemotherapy, 1964, pp. 33-37.

Jones, R. N. et al., In vitro Gram-positive antimicrobial activity of evernimicin (SCH 27899), a novel oligosaccharide, compared with other antimicrobials: a multicentre international trial, Journal of Antimicrobial Chemotherapy, 47, 15-25, 2001.

* cited by examiner

*Primary Examiner* — Traviss C McIntosh, III

(74) *Attorney, Agent, or Firm* — David J. Kerwick

(57) ABSTRACT

This invention relates to methods of treatment and prevention of mastitis in animals by orthosomycin antimicrobial compounds.

15 Claims, 1 Drawing Sheet

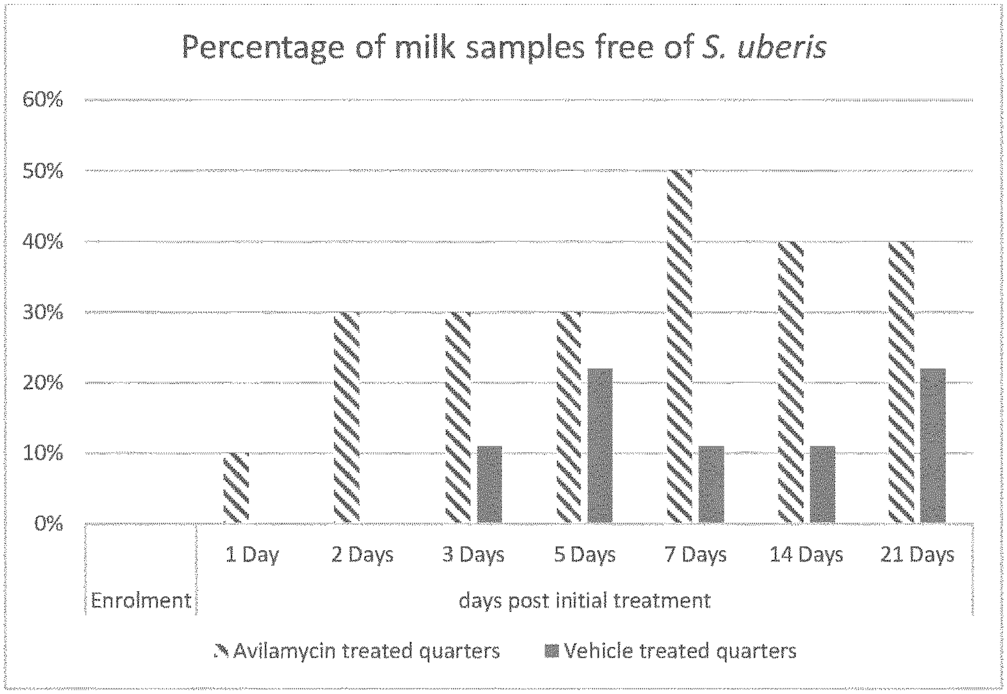
Percentage of quarters free of *S. uberis* after treatment with avilamycin (n=10) and vehicle (n=9) over the observation period.
At enrollment prior to treatment milk of both treatment groups contained a mean *S. uberis* count of 1-2 x $10^{E7}$/ml.

METHODS OF TREATING MASTITIS WITH AN ORTHOSOMYCIN ANTIMICROBIAL COMPOUND

CROSS-REFERENCE TO RELATED APPLICATIONS

This is a U.S. National Phase entry under 35 U.S.C. § 371 of International Patent Application No. PCT/EP2021/087444, filed Dec. 23, 2021, which published as WO2022/136622 on Jun. 30, 2022, which claims priority to EP Application Serial No. 20217194.8, filed Dec. 24, 2020; the content of each of which is hereby incorporated by reference in its entirety.

TECHNICAL FIELD

This invention relates to compounds for use in methods of treatment and prevention of mastitis in animals.

BACKGROUND

Mastitis is one of the most serious problems of the dairy industry that impacts milk production, composition and quality and animal welfare.

Mastitis is an inflammation of the mammary gland and is often caused by pathogens that pass through the teat canal. Despite preventive care by selective breeding, milking technology and hygiene measures, it is often impossible to prevent infections, most of which are caused by bacterial pathogens.

There are two major periods during which this can occur: during the lactation period or during the non-lactation (dry) period.

During the lactation period invasion of the teat usually occurs during milking. After milking, the teat canal remains dilated for 1-2 hours while the canal of a damaged teat may remain partially open permanently. This makes it easier for pathogens from the environment or those found on injured skin to enter the teat canal. Adherence of such pathogens to tissues lining cisterns and ducts may prevent flushing-out during milking and help establish infections.

At the conclusion of the lactation period and once milking has stopped for the season the teat canal is closed by the formation of a natural keratin teat plug. This is the so called dry period and the animal is called a “dry cow”. This typically happens over a period of 2-3 weeks. However, prior to the formation of this teat plug the teat canal is open and highly susceptible to bacterial infection. It can also be the case that if the teat plug is poorly developed there is an opportunity for on-going infection.

Mastitis treatment is therefore typically administered at two different stages in the cow’s lactation cycle: the dry period or dry cow (DC) stage and the lactation period or milking or lactating cow (LC) stage.

To treat existing infections in a lactating animal a mastitis treatment needs to be either intramammary administered between the milking or parenterally with antimicrobials that reach the mammary gland systemically via the blood. To prevent new cases of mastitis during the dry period conventional antimicrobial products or a teat sealant product or a combination of both are generally used.

Several antimicrobial products are known and commercially available for use in both periods. However alternative treatment options are desirable.

A recurring problem with existing antimicrobials that are used in the prior art for the treatment of mastitis is that the pathogens may develop resistance towards the antimicrobials. Therefore, new active pharmaceutical ingredients are important for novel and sustainable solutions for mastitis treatment.

International patent application WO2014/121343 describes the intramammary administration of polyether ionophore antimicrobials for the treatment or prevention of mastitis.

The present invention has the object of providing effective compounds for such treatments in one of the periods or both periods, that are active against the main bacterial causes of mastitis and are suitable to treat and/or prevent mastitis. Preferably the compounds are also active against resistant strains of these bacterial pathogens. The current invention addresses these needs.

SUMMARY OF INVENTION

According to one aspect of the invention there is provided an orthosomycin antimicrobial compound for use in a method for treatment or prevention of mastitis in an animal.

According to another aspect of the invention, there is provided a pharmaceutical composition comprising a therapeutically effective amount of at least one orthosomycin antimicrobial compound and a pharmaceutically acceptable carrier for use in a method for the treatment or prevention of mastitis in an animal.

In a particular embodiment the orthosomycin antimicrobial compound is the sole antimicrobial compound in such a pharmaceutical composition.

The administration may be by intramammary administration, such as by intramammary injection or infusion via the teat canal.

Further features of the invention provide for the orthosomycin antimicrobial compound to be selected from the group comprising evernimicin and avilamycin.

In one preferred embodiment the animal may be a lactating cow. In another preferred embodiment the animal is a dry cow.

According to another aspect of the invention, there is provided an intramammary injector comprising an orthosomycin antimicrobial compound as the sole antibiotic active ingredient in a pharmaceutically acceptable carrier.

BRIEF DESCRIPTION OF THE DRAWINGS

FIG. 1. Shows the percentage of quarters free of *S. uberis* after treatment with avilamycin (n=10) and vehicle (n=9) over the observation period.

DETAILED DESCRIPTION

General

Before describing the present invention in detail, it is to be understood that the invention is not limited to particular exemplified methods or compositions disclosed herein. It is also to be understood that the terminology used herein is for the purpose of describing particular embodiments of the invention only and is not intended to be limiting.

In addition, the carrying out of the present invention makes use of, unless otherwise indicated, conventional microbiological techniques within the skill of the art. Such conventional techniques are known to the skilled worker.

As used herein, and in the appended claims, the singular forms “a”, “an”, and “the” include the plural unless the context clearly indicates otherwise.

Throughout this specification, unless the context requires otherwise, the word "comprise" or variations such as "comprises" or "comprising", will be understood to imply the inclusion of a stated integer or group of integers but not the exclusion of any other integer or group of integers.

The invention described herein may include one or more ranges of values (e.g. size, concentration, dose etc.). A range of values will be understood to include all values within the range, including the values defining the range, and values adjacent to the range that lead to the same or substantially the same outcome as the values immediately adjacent to that value which define the boundary of the range.

Definitions

In general, the term "therapeutically effective amount" as used herein, refers to a nontoxic but sufficient amount of the composition to provide the desired biological, therapeutic, and/or prophylactic result.

That is, reference to the administration of the therapeutically effective amount of orthosomycin antimicrobial compounds refers to a therapeutic effect in which its bactericidal compounds in order to correlate enzyme inhibition with growth inhibition of desired pathogenic bacteria.

A therapeutically effective amount in any individual case may be determined by one of ordinary skill in the art using routine experimentation.

The inventors found that orthosomycin antimicrobial compounds can be successfully used to treat or prevent mastitis in animals. It has been found that representative orthosomycin antimicrobial compounds successfully inhibit mastitis causing bacterial pathogens and diminish the clinical signs of mastitis.

Orthosomycins are oligosaccharide molecules containing two orthoester saccharide linkages. Many known orthosomycins have antimicrobial activity. The term "antimicrobial compound" refers to compounds that have either bactericidal or bacteriostatic activity against certain bacteria. Therefore, orthosomycins are sometimes called orthosomycin antimicrobial compounds.

The general structure of orthosomycins is illustrated below. The saccharide residues in the above orthosomycin are labeled A-H and the key features of orthosomycins, the orthoester linkages are indicated below.

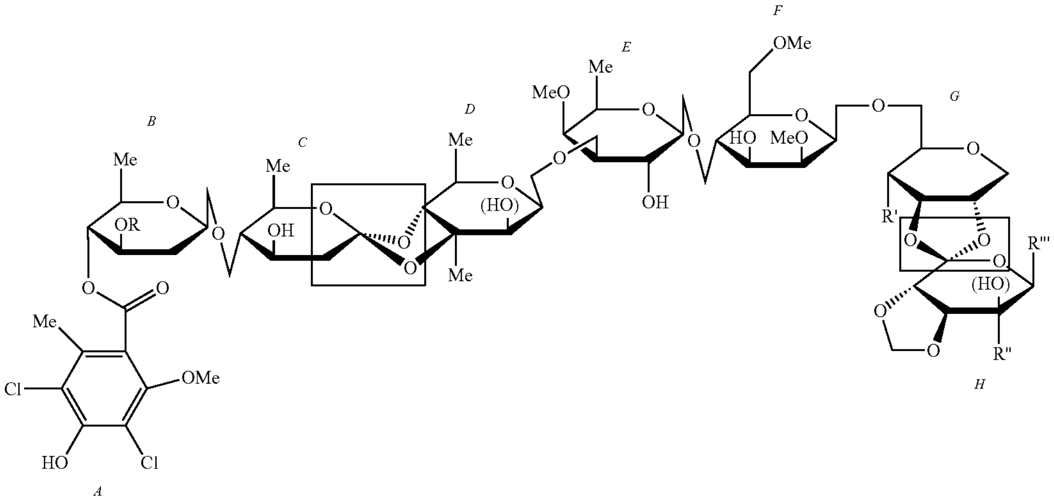

or bacteriostatic activity causes a substantial inhibition of pathogens in the udder of a treated animal.

This means sufficient amount of the compound to treat or prevent mastitis and the bacterial infections with pathogens that are causing mastitis, at a reasonable benefit/risk ratio applicable to any veterinary treatment.

A bactericide or bacteriocide, is an antibiotic substance which kills bacteria, including desired target mastitis causing pathogens. Bacteriostatic means that an antibiotic compound is capable of inhibiting the growth or reproduction of (desired target pathogenic) bacteria.

The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the (desired target pathogenic) bacteria in the population are reduced or the population even eliminated. If an enzyme activity assay is used to screen for inhibitors, one can make modifications in uptake/efflux, solubility, half-life, etc. to Known orthosomycin compounds can broadly be classified into two classes: (1) the everninomicins that contain an amino- or nitrosugar residue in the terminal position of the oligosaccharide chain, i.e. wherein R is evernitrose in the above molecule; and (2) the avilamycins, curamycins and flambamycins that do not contain an amino- or nitrosugar residue in the terminal position, i.e. wherein R is hydrogen in the above molecule. Within the second class of orthosomycins, the avilamycins and the curamycins differ only in the nature of the acyl side chain found in ester linkage to the C45-hydroxyl group of sugar residue G. Neither the avilamycins nor the curamycins carry a simple methyl group on this hydroxyl. Flambamycins differ from the avilamycins only at position C23 of sugar residue D, w which has a methylsubstitution in the avilamycins but carries an additional hydroxyl group on the flambamycins. The eveminomicins may or may not carry a hydroxyl at this position.

A preferred orthosomycin antimicrobial compound is avilamycin with the CAS number 69787-79-7.

Avilamycin is an orthosomycin antibiotic complex produced by the fermentation of *Streptomyces viridochromo-*

*genes*. Avilamycin is intended for use as a veterinary medicine in chickens, turkeys, pigs and rabbits to control bacterial enteric infections. It exhibits good antimicrobial activity against important veterinary Gram-positive pathogens (e.g., *Clostridium perfringens*) and has no related molecules in its class in human use. Therefore, avilamycin has been developed for treating necrotic enteritis in poultry, and enteric disease in pig and rabbits.

Another preferred orthosomycin antimicrobial compound is evernimicin with the CAS number 109545-84-8.

Evernimicin is an oligosaccharide orthosomycin antibiotic which binds to the large ribosomal subunit 50S. Evernimicin can be obtained by fermentation from *Micromonospora carbonaceae* (see i.a. Chu et al. J. Nat. Prod. 2002, 65, 1588-1593 or Wagman et al. Antimicrobial agents and chemotherapy 1964, 10, 33-37).

The chemical structure of evernimicin is depicted in the following:

exposes the compound to milk. Avilamycin as representative of the orthosomycin antimicrobial compounds maintained its activity in milk and Example 3 confirms that it inhibits in vivo important mastitis causing pathogens. Therefore, these compounds were found to be useful for the treatment of mastitis.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above. For example, in the treatment of mastitis, the treatment completely or partially removes or prevents the signs of mastitis.

Types of animals that may benefit from the practice of the invention include any that are susceptible to infection by an etiological agent of mastitis. Suitably the animal that is treated according to the invention is a female mammal.

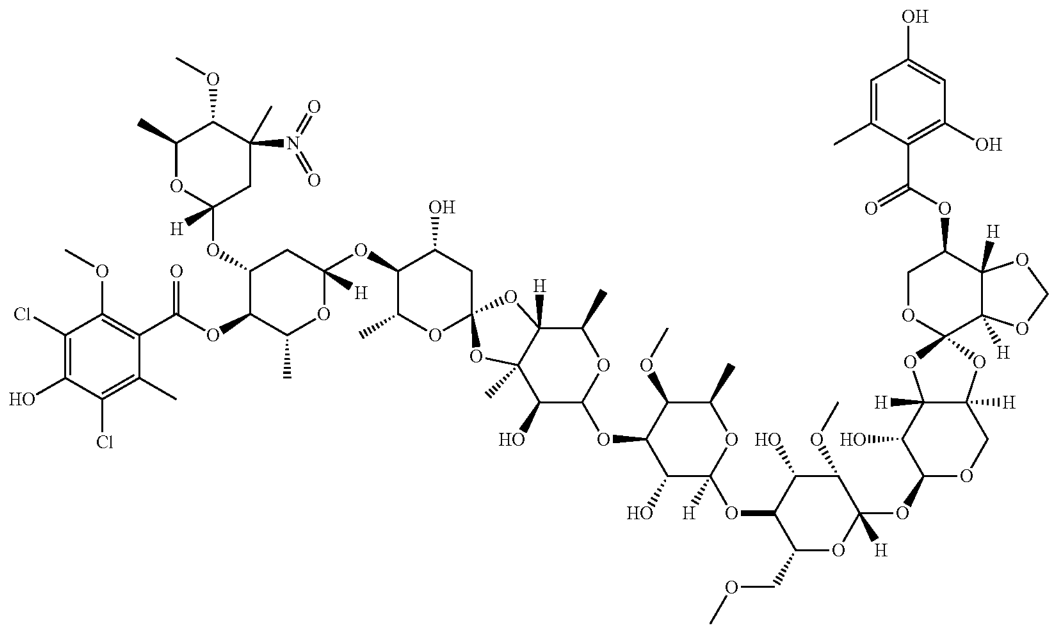

Manufacturing processes to obtain evernimicin have been described in prior art.

The compounds of this invention exhibit unexpectedly high antibacterial activity against *Staphylococcus* spp., *Streptococcus* spp, and/or *Trueperella pyogenes*. For example, representative compounds (avilamycin and evernimicin) were tested against coag, neg. Staph, *Staphylococcus* spp., *Streptococcus* spp, and/or *Trueperella pyogenes*. using the conventional broth-dilution assay and milk. The minimal inhibitory concentrations (MIC's) of representative compounds against these species are summarized in Table 1 and 2.

It has been surprisingly found that the polyether ionophore antimicrobials of prior art International patent application WO2014/121343, such as salinomycin, lasalocid and monensin that were active against different *S. aureus* isolates in bacteriological broth lost any activity when investigated in milk as shown in Table 4.

The maintenance of the antibacterial effect in milk is an important requirement for a successful use for the treatment or control of mastitis after intramammary administration that Exemplary animals include but are not limited to members of the biological subfamily Bovinae which includes medium- to large-sized ungulates such as domestic cattle, bison, African buffalo, the water buffalo, etc. The animals may be so-called livestock raised in an agricultural setting for the production of dairy products; or may be raised to perform work; or may be in another setting, e.g. in a zoo, animal reserve, etc., or raised for some other reason, e.g. as pets, show animals, for breeding purposes, etc.

Especially preferred is the use of the compounds of the current invention in dairy cows that are used for milk production.

Other exemplary animals that can be treated with the compounds and compositions of the current invention are small ruminants, such a sheep or goats or pseudoruminants, such as e.g., camels or lamas.

According to the treatment by the compounds of the present invention and/or embodiments thereof, bacterial infections are treated or prevented in an animal by administering to the animal a therapeutically effective amount of a compound of the invention, in such amounts and for such time as is necessary to achieve the desired result. It will be understood, however, that the total daily usage of the compounds and compositions of the present invention will be decided by the attending veterinarian within the scope of sound medical judgment.

The orthosomycin antimicrobial compound is administered to the mammary gland (two or four of which form the udder in a ruminant) of the animal at a dose selected from the group comprising 5 mg/gland to 2,000 mg/gland, preferably 20 mg/gland to 900 mg/gland, more preferably 40 mg/gland to 600 mg/gland, most preferably 50 mg/gland to 500 mg/gland.

In one embodiment of the invention, the orthosomycin antimicrobial compound is administered to the animal at a total dosage per teat canal (mammary gland) selected from the group consisting of between 1 mg to 1000 mg; between 10 mg and 500 mg; between, 10 mg and 400 mg; between 10 mg and 300 mg; between 10 mg and 200 mg; between 10 mg and 10 0 mg; and between 5 0 mg and 100 mg.

In one embodiment of the invention, the orthosomycin antimicrobial is administered to each mammary gland via the teat canal, i.e. intramammarily using an intramammary device, such as an intramammary injector/syringe. This is a preferred route in the treatment of mastitis in ruminants.

It has been surprisingly found (see Example 3) that the intramammary administration of orthosomycin antimicrobial compound avilamycin did not result in systemic blood concentrations of the compound. It will be understood that systemic exposure of a subject to be treated according to the methods of treatment of the invention is to be minimized in order to minimize systemic side effects of exposure to therapeutically effective amounts of orthosomycin antimicrobial compound.

It will be appreciated that the mammary/blood barrier functions as a physical barrier to absorption of therapeutically effective amounts of oligosaccharide orthosomycin antimicrobial which compounds are found to remain localized within the tissues and fluids of the mammary gland for localized antimicrobial activity and reduced toxic effects.

In one embodiment the mastitis is caused by *Staphylococcus* spp., *Streptococcus* spp, and/or *Trueperella* spp. pathogens.

In particular, the mastitis may be caused by pathogens selected from *Staphylococcus aureus*, coagulase-negative staphylococci, *Streptococcus uberis, Streptococcus dysgalacticae* and/or *Streptococcus agalacticae* or by infections by more than one of these pathogens.

Furthermore, the mastitis may be caused by *Trueperella pyogenes*. Also, the mastitis may be caused by *Corynebacterium bovis.*

Most preferably, the bacterial agent is an antimicrobial-sensitive strain or an antimicrobial resistant strain. Examples of antimicrobial-resistant strains include MRSA and tetracycline resistant *Streptococcus* spp. In a preferred embodiment, the bacterial agent is MRSA.

In one embodiment, the bacterial agent is selected from the group comprising, but not limited to, coagulase-negative staphylococci (CNS).

In another embodiment, the bacterial agent is selected from coagulase-positive staphylococci.

In a most preferred embodiment, the bacterial agent is *Staphylococcus aureus.*

In another embodiment, the bacterial agent is from the *Streptococcus* genus. For example, the bacterial agent may be selected from the group comprising, but not limited to, *Streptococcus uberis, Streptococcus agalactiae, Streptococcus dysgalactiae, Streptococcus pyogenes, Streptococcus bovis. The bacteria may be isolated from bovine mastitis.*

In another embodiment, the bacterial agent is from the *Bacillus* genus. For example, the bacterial agent may be selected from the group comprising, but not limited to, *Bacillus melaninogenicus, Bacillus pumilus, Bacillus licheniformis, Bacillus cereus, Bacillus subtilis*. The bacteria may be isolated from bovine mastitis.

In some embodiments, one or more, preferably one orthosomycin antimicrobial compound is used to treat mastitis caused by infection by a pathogen, that is resistant to one or more other conventional antimicrobial compounds. In some embodiments, the compound according to this invention is active against a pathogen, that is resistant to one or more of macrolide antibiotics, aminoglycosides, fluoroquinolones, or beta lactams, cephalosporins, especially one or more selected from the group of cefquinome, ceftiofur or penicillins.

In general, intramammary infections by such mastitis causing pathogens may result in subclinical or clinical mastitis in infected animals.

In one embodiment orthosomycin compounds or pharmaceutical compositions according to the invention are used in the treatment or prevention of mastitis, especially bovine mastitis, wherein the mastitis is a subclinical mastitis.

Subclinical mastitis encompasses an infection without apparent signs of local inflammation or systemic involvement and may result in transient episodes of abnormal milk or udder inflammation, which are usually asymptomatic.

Therefore, identifying affected animals early in the course of mastitis is difficult. Detection may be carried out by examination of milk for somatic cell counts using standard tests known in the art such as the California Mastitis Test. Somatic cell counts generally indicate the presence of infection. The causative agent of the infection may be identified by bacterial culture of milk according to standard procedures known in the art.

In one embodiment orthosomycin compounds or pharmaceutical compositions according to the invention are used in the treatment or prevention of mastitis, especially bovine mastitis, wherein the mastitis is a clinical mastitis.

Clinical mastitis (also called clinically manifest mastitis) encompasses an inflammatory response to infection causing visibly abnormal milk. Indications of inflammation may include changes in the udder (swelling, heat, pain, redness). Mild clinical cases include local signs only. Severe clinical cases include systemic involvement (fever, anorexia, shock) and rapid onset.

Preferred is the treatment or prevention of clinically manifest mastitis.

Mastitis treatment is typically administered at two different stages in the cow's lactation cycle: the dry cow (DC) stage and the milking or lactating cow (LC) stage.

Dry Cow Therapy

Dry cow therapy is administered to a dry cow i.e. to a cow that is no longer milked during the approximate 4-week to 10-week period of time immediately preceding the delivery of a calf.

Dry cow therapy is administered in order to remove those infections accumulated during the lactation stage, to prevent carry over to the next lactation, and to reduce the number of new infections contracted during the dry period.

Infections may already be present in the udder at drying-off or may gain access during the dry period and may be carried over into the subsequent lactation causing clinical or subclinical mastitis.

Therefore, in the prior art so-called dry cow treatments have been performed widely. This dry cow treatment is therefore is a prevention of mastitis (that would otherwise appear in the next lactation). Dry cow products with a good local tolerance, a sufficient broad spectrum and duration of activity are desired.

The infusion of antibacterial agents into each quarter immediately after the last milking of the lactation, in order to treat existing infections and to afford prophylaxis against new infections has been practiced for many years.

Dry cow treatment may be carried out by administration of antimicrobial products or the intramammary application of a teat sealant or a combination of both treatments. The antimicrobial product is conventionally administered via a syringe that is partially inserted into the teat canal and the antimicrobial is massaged up the teat and into and throughout the gland cistern.

Prevention of mastitis is reliant on sufficient antimicrobial being retained in the teat canal to kill off any bacteria that may enter the teat canal over the dry period. To prevent new infections during the dry period, the cow's natural defense mechanism includes the formation of a natural keratin plug which seals the teat. The keratin plug provides an effective barrier to the ingress of bacteria from the teat canal during the dry period. Delay in or outright failure to naturally form a complete keratin plug during the dry period puts the cow at risk of experiencing new mastitis infections.

Pharmaceutical compositions for the treatment of existing pathogen infections or prevention of mastitis in dry cows at the end of lactation (i.e. beginning of the dry period), and hence prevention of mastitis in the following lactation may further comprise excipients intended for gelling or otherwise solidifying the formulation and sealing the teat canal and/or include an agent that stimulates the formation of the keratin plug.

Effective dry cow treatment requires intramammary preparations that allow sustained and effective intramammary concentrations of antibacterial agents for a prolonged period, preferably throughout the dry period. For example, the persistence of insoluble salts of penicillin (especially cloxacillin benzathine) formulated in a gel of aluminum monostearate and diluted in mineral oil. A method of supplementing the teat's natural defenses, and to ensure that the canal is sealed efficiently throughout the entire dry period, is by the use of an internal teat sealant.

The use of an internal teat sealant is known, and commercial products are available such as e.g. Orbeseal of Zoetis.

Most commonly the internal teat seal is a bismuth salt in a base that is infused into the teat canal at drying off. It has no antibacterial properties and hence strict hygiene during administration is essential. However, inclusion of antimicrobial substances within the internal teat seal composition can treat existing infections and enhance the likelihood of prevention of new infections.

The composition may be in the form of a teat sealant comprising an orthosomycin antimicrobial compound as described herein, together with gelling substance such as those commonly used in the art.

For example, bismuth subnitrate 65% (w/w) in a paraffin oil gel base, or bismuth subnitrate, liquid paraffin, aluminum stearate and a gel base.

In one embodiment of the invention, the orthosomycin antimicrobial is administered to a dry cow using a dosing regimen of once per dry period, or twice per dry period.

Lactating Cow Therapy

Lactating cow therapy is administered to lactating cows, i.e. to cows that are in milk, this means they are regularly milked, at least once per day.

Formulation of lactating cow preparations seeks to balance two opposing factors. The formulation must provide effective concentrations of the antimicrobial compound throughout the mammary gland wherever the infecting agents are present (i.e. the site of infection) for as long as possible, even in the face of continued milking twice or more frequently each day while minimizing the period that milk must be withheld due to persistence of unacceptable concentrations of antimicrobial compound residues in the milk after the a antimicrobial product has been administered.

In general, preparations for use in lactating cows provide high concentrations for hours or days and are formulated in quick release aqueous or oil (mineral or vegetable) bases.

Pharmaceutical compositions for the treatment of mastitis in lactating animals, especially cows may further comprise excipients intended for rapid release such that a formulation that is not retained in the mammary gland of the lactating animal/cow.

Preferably, in lactating animals such as lactating cows the orthosomycin antimicrobial is administered via the teat canal to each infected quarter or half of the subject's mammary gland (such as an udder), immediately following milking.

For example, if the animal is s milked twice daily, the orthosomycin antimicrobial is administered immediately after each milking.

In a preferred embodiment, the orthosomycin antimicrobial is administered to the subject during lactation twice daily, immediately after each milking for 2 days, 3 days, 7 days, 14 days, 21 days and one month, or until the signs of mastitis are no longer detectable; or, in the case of application to bovines, to cows when they are dried off at the end of lactation.

According to another aspect of the invention, there is provided a method of treating mastitis in an animal, the method including the step of administering a pharmaceutical composition comprising a therapeutically effective amount of an orthosomycin antimicrobial compound to the mammary gland of the animal that shows signs of clinical mastitis, carries mastitis causing pathogens in the milk or is at risk of infection by such mastitis causing pathogens.

According to another aspect of the invention, there is provided a method of preventing mastitis in an animal, the method including the step of administering a pharmaceutical composition comprising a therapeutically effective amount of an orthosomycin antimicrobial compound to the mammary gland of the animal.

According to another aspect of the invention, there is provided the use of an orthosomycin antimicrobial compound in the manufacture of a medicament for the treatment or prevention of mastitis in an animal.

Generally, the orthosomycin antimicrobial compounds are administered in a pharmaceutical composition. In a preferred embodiment the pharmaceutical composition is specifically adapted to intramammary administration.

The orthosomycin antimicrobial compound may be administered in various dosage forms. The term "dosage form" means that the compounds according to this invention are formulated into a product suitable for administering to the animal via the envisaged dosage route. Such dosage forms are sometimes referred to herein as formulations or pharmaceutical composition.

Such pharmaceutical compositions comprise the orthosomycin antimicrobial compound and a pharmaceutically acceptable carrier that facilitates the administration to the animal.

As used herein, the term "pharmaceutically acceptable carrier" means a non-toxic, inert semi-solid or liquid filler, solvent, diluent, encapsulating material excipient or formulation auxiliary of any type.

The carrier is selected so as to be non-toxic, veterinary acceptable, compatible with the orthosomycin antimicrobial compound, and of a viscosity to permit administration, using a syringe/intramammary injector at ambient temperature, whilst controlling the release characteristics of the compound.

The veterinary composition according to the current invention may further comprise additional pharmaceutical excipients known in the art. Such pharmaceutical excipients are e.g. described in "Gennaro, Remington: The Science and Practice of Pharmacy" (20. Edition, 2000), incorporated by reference herein.

Pharmaceutical compositions for use in the present invention can be in the form of liquid solutions, emulsions, or suspensions, or semisolid formulations such as e.g. gels, pastes, or other forms known in the art, especially for intramammary administration.

The current invention discloses in pharmaceutical composition comprising 1 to 30% by weight of the orthosomycin antimicrobial compound. Preferably the pharmaceutical composition comprises 2 to 15%, most preferred 4 to 10% by weight of the orthosomycin antimicrobial compound, especially avilamycin. By "by weight" in this patent application it is meant a percentage by weight of the total composition.

The pharmaceutical compositions of the invention may be in the form of thickened (or viscosity modified) solutions, gels, ointments, suspensions, pastes, or any other suitable dosage form. For example, the formulation may be a gel, which is safe and easy to administer to and through the teats of a dairy cow.

The viscosity of such a gel may be adjusted by any veterinarily or pharmaceutically safe and effective rheology/viscosity modifier. In an embodiment, the veterinary gel may be thixotropic, in that its viscosity decreases when shear force is applied (e.g. squeezing a tube of toothpaste allows the paste to flow). Thus, in an embodiment, the compositions may be shear thinning.

In cases where the composition is administered to dairy cattle at the end of lactation (i.e. beginning of the dry period), it may be desirable to include an agent that stimulates the formation of the keratin plug.

In cases where the cow's teat sphincter muscle is compromised, compositions somewhat higher viscosities may be used to improve retention in the mammary gland.

The antimicrobial orthosomycin antimicrobial compound may also be added to other currently known, or yet to be developed, dry period paste- or gel compositions. The viscosity of the compositions may be measured, for example, using a Brookfield LV-E digital viscometer; different measurement speeds may be used.

The composition may also be thickened to the point where it is considered a "paste." A paste consistency may be achieved by adding a sufficient amount of silica, or other suitable thickening material. Mucoadhesive and paste-forming agents may facilitate longer udder-retention times, in particular, for the "dry cow" application. In a particular embodiment, the mucoadhesive agent may be a cross-linked acrylic acid-based polymer, polycarbophil, chitosan (or derivatives thereof, such as trimethylated chitosan), polyethylene oxide, or combinations thereof.

In an embodiment, the paste composition may comprise at least one non-toxic heavy metal salt, including bismuth subnitrate. A suitable paste may also comprise a gel base (comprising liquid paraffin), aluminum stearate and silicon dioxide. Fumed silica, such as AEROSIL®, is a particularly useful TRM and thixotropic agent. However, any pharmaceutically or veterinarily acceptable fumed metal oxide may be used in the practice of the invention.

In a particular embodiment, the rheology modifier may be selected from 12-hydroxystearin (THIXCIN®), aluminum stearate, cellulose derivatives (e.g. hydroxypropyl cellulose (HPC); hydroxypropyl methyl cellulose (HPMC); hydroxyethyl cellulose (HEC); ethyl cellulose (EC N50)), beeswax, hydrogenated peanut oil, castor oil, hard/soft paraffin, metal salts of fatty acids, and combinations thereof.

The compositions described herein may be in the form of a liquid formulation. The liquid formulation may comprise a solution that includes a therapeutic agent, such as an orthosomycin antimicrobial compound, especially avilamycin dissolved in a solvent.

Generally, any solvent that has the desired effect may be used in which such therapeutic agent dissolves and which can be administered to a subject.

Generally, any concentration of therapeutic agent that has the desired effect can be used. The formulation in some variations is a solution which is unsaturated, a saturated or a supersaturated solution.

The solvent may be a pure solvent or may be a mixture of liquid solvent components. In some variations the solution formed is an in-situ gelling formulation.

Solvents and types of solutions that may be used are well known to those versed in such drug delivery technologies.

The pharmaceutical composition may be a suspension, preferably an aqueous suspension comprising the therapeutic agent, especially an orthosomycin antimicrobial compound, especially avilamycin particles having an effective average particle size of less than about 450 nm, and optionally a surfactant.

The effective average particle size of the orthosomycin antimicrobial compound, especially avilamycin may be less than about 450 nm or less than 400 nm, less than about 350 nm, or less than about 300 nm.

In another embodiment the effective average particle size of the orthosomycin antimicrobial compound, especially avilamycin is less than about 250 nm less than about 200 nm.

In one embodiment the effective average particle size of the orthosomycin antimicrobial compound, especially avilamycin is between about 50 nm and 450 nm about 100 nm and 400 nm or between about 150 and 350 nm.

As used herein, particle size refers to a number average particle size as measured by conventional particle size measuring techniques well known to those skilled in the art, such as laser scattering, sedimentation field flow fractionation, photon correlation spectroscopy, or disk centrifugation.

The particle size measurement can be performed with a Malvern Mastersizer 2000 with the Hydro 20000 measuring cell, or with a Horiba LA-910 laser scattering particle size distribution analyzer.

By "an effective average particle size of less than about 450 nm" it is meant that at least 90% of the particles have a weight average particle size (D90) of less than 450 nm when measured by the above-noted techniques.

Methods of preparing pharmaceutical compositions are well known in the art and are disclosed, for example, in Remington: The Science and Practice of Pharmacy, Mack Publishing Company, Easton, Pa., 20th Edition (2000).

Although the orthosomycin antimicrobial compound, especially avilamycin is preferably the sole antibiotic in the pharmaceutical composition according to the invention (this means no other antimicrobial compound, except components that have besides their normal function as excipient a limited antibacterial/disinfectant effect such as e.g. acriflavine dye etc.), the orthosomycin antimicrobial compound can be co-administered with other therapeutic agents that are selected for their particular usefulness against the condition that is being treated.

In one embodiment the orthosomycin antimicrobial compound is the sole antibiotic, having significant bactericidal or bacteriostatic properties, and at least one additional non-antibiotic pharmacologically active component aimed at treatment of mastitis is included in the mastitis treatment.

Such component can be e.g., a specific or non-specific immunostimulant or a probiotic, a bacteriocin, a bacteriophage or a bacteriophage cocktail, phage endolysins or any other component that positively influences the body defence mechanism of the target animal.

Such immunostimulant or non-antibiotic can be present in the same pharmaceutical composition. Alternatively, the immunostimulant or non-antibiotic can be administered to the target animal in parallel to the orthosomycin compound or following or preceding the orthosomycin compound administration as part of a treatment regimen.

Such immunostimulant or non-antibiotic can be administered to the animal locally (e.g. topically or by intramammary infusion) or systemically, such as orally or by injection.

Contemplated other active ingredient(s) that may be administered in combination with the compounds of the current invention include, for example, anti-inflammatories, dermatological preparations (e.g. antiseptics and disinfectants), and immunobiologicals (e.g., vaccines and antisera) for disease prevention.

Combination means that the co-administered active ingredient(s) is administered in a common formulation with the orthosomycin antibacterial compound, especially avilamycin.

Alternatively, the co-administered active ingredient(s) is administered to the animal in parallel (not more than approximately 30 minutes apart) from the orthosomycin antibacterial compound.

The current invention proves a method of treating or preventing mastitis in a female mammal, preferably a non-human mammal, preferably a cow, sheep, camel or goat, preferably a cow.

The invention is further directed to the use of orthosomycin antimicrobial compound for use in the manufacturing a medicament for treating or preventing mastitis in an animal.

The orthosomycin antimicrobial compound is preferably avilamycin, or evernimicin and is administered intramammarily, especially a therapeutically effective amount of the orthosomycin antimicrobial compound is administered to the mammary gland of a cow.

The animal in need of treatment of mastitis, clinical or subclinical mastitis is preferably a lactating mammal, preferably a lactating cow.

Preferably a therapeutically effective amount of the orthosomycin antimicrobial compound is administered to the mammary gland of a cow, preferably to a cow with clinically manifest mastitis, preferably when the mastitis is caused by *Staphylococcus* spp., *Streptococcus* spp, and/or *Trueperella pyogenes.*

The animal in need of prevention of mastitis, clinical or subclinical mastitis is preferably an animal at the end of lactation, at drying of, mammal, preferably a dry cow, especially when the animal has, or is at risk for an infection by *Staphylococcus* spp., *Streptococcus* spp, and/or *Trueperella pyogenes.*

The orthosomycin antimicrobial compound may be administered in parallel with an additional non-antibiotic pharmacologically active component that is aimed at treatment of mastitis.

Such additional non-antibiotic pharmacologically active component may be a specific or non-specific immunostimulant or a probiotic, a bacteriocin, a bacteriophage or a bacteriophage cocktail, phage endolysins or any other component that positively influences the body defence mechanism of the animal.

Another aspect of the current invention is an intramammary injector comprising an orthosomycin antimicrobial compound as the sole antibiotic active ingredient in a pharmaceutically acceptable carrier.

An intramammary injector or syringe is a device that is used to insert the material directly into the teat canal via the opening at the base of the teat. The cannula of the injector/syringe is very elastic and does not injure the teats of the udder.

The pharmaceutical composition comprising an orthosomycin antimicrobial compound as the sole antibiotic active ingredient in a pharmaceutically acceptable carrier may be filled into the injector or syringe packs of the conventional type for intramammary administration, i.e. provided with a cannula nozzle for insertion into the teat to allow extrusion directly into the mammary gland via the teat canal.

Alternatively, the pharmaceutical composition comprises another antibiotic compound, as described below.

If there is an additional antibiotic present, the pharmaceutical composition may comprise a antibiotic, that is classified by the Antimicrobial Advice ad hoc Expert Group (AMEG) 2018 of the European Union in category D ("Prudence") which is the lowest risk category. Examples are aminopenicillins, without beta-lactamase inhibitors such as e.g. amoxicillin, ampicillin; cyclic polypeptides such as bacitracin; nitrofuran derivatives such as furazolidone; nitroimidazoles such as metronidazole; penicillins: anti-staphylococcal penicillins, (beta-lactamase-resistant penicillins) such as cloxacillin; penicillins: natural, narrow spectrum penicillins (beta-lactamase-sensitive penicillins) such as benzylpenicillin, phenoxymethylpenicillin; aminoglycosides: spectinomycin; steroid antibacterials such as fusidic acid; sulfonamides, dihydrofolate reductase inhibitors and combinations such as sulfadiazine, trimethoprim; or tetracyclines such as oxytetracycline or doxycycline.

If there is an additional antibiotic present, the pharmaceutical composition may comprise an antibiotic that is new or not classified by the Antimicrobial Advice ad hoc Expert Group (AMEG) 2018 of the European Union.

A single dose will normally contain 1 to 10 grams, preferably 3 to 8 grams of the composition.

In a preferred embodiment the intramammary injector comprises 25 to 1000 mg of the orthosomycin antimicrobial compound.

In another preferred embodiment the intramammary injector comprises a teat seal formulation for forming a physical barrier in the teat canal of a dry cow.

EXAMPLES

Example 1 In Vitro Antibacterial Activity of Avilamycin Against Cow Mastitis Pathogens Antimicrobial activity of avilamycin was determined against cow mastitis causing pathogens.

Methods

Minimal inhibitory concentrations (MIC) were determined in bacteriological broth according to Clinical and Laboratory Standard Institute (CLSI) guideline VET01-A4 [1]. The MIC results were interpreted according to the CLSI document VET01-S3 [2].

For MIC determination in milk, the in vitro activity was determined by measuring the minimum inhibitory concentrations (MIC) according to CLSI document VET01-A4 [1] using full cream UHT milk as test medium. About 2 h before the end of the incubation 10 μL of alamar Blue® was added to each well of the microdilution trays, resulting in a final concentration of 10% of alamar Blue®. Blue color of the medium indicated no living cells (no bacterial growth) red/pink to white color of the medium indicated living cells (bacterial growth). The MIC results were interpreted according to the CLSI document VET01-S3 [2].

Results

Good antimicrobial activity of avilamycin and evernimicin against mastitis-causing pathogens was determined (Tabs. 1, 2).

TABLE 1

Antibacterial activity of avilamycin against mastitis-causing pathogens.

| MIC in μg/mL | *S. aureus* | coa-neg *Staph.* | *Strep. agalactiae* | *Strep. dysgalactiae* | *S. uberis* | *Truep. pyogenes* |
|---|---|---|---|---|---|---|
| ≤0.063 | | | 17 | 1 | | 29 |
| 0.125 | | | 13 | 23 | 1 | 1 |
| 0.25 | | | | 5 | 12 | |
| 0.5 | | | | | 17 | |
| 1 | 5 | 4 | | | | |
| 2 | 19 | 13 | | | | |
| 4 | 26 | 11 | | | | |
| 8 | | 1 | | | | |
| 16 | | | | | | |
| 32 | | 1 | | | | |
| 64 | | | | | | |
| >64 | | | | | | |
| Total tested | 50 | 30 | 30 | 29 | 30 | 30 |
| Minimum MIC | 1 | 1 | ≤0.063 | ≤0.063 | 0.125 | ≤0.063 |
| Maximum MIC | 4 | 32 | 0.125 | 0.25 | 0.5 | 0.125 |
| $MIC_{50}$ | 2 | 2 | ≤0.063 | 0.125 | 0.5 | ≤0.063 |
| $MIC_{90}$ | 4 | 4 | 0.125 | 0.25 | 0.5 | ≤0.063 |

MIC: minimum inhibitory concentration.

TABLE 2

Antibacterial activity of evernimicin against mastitis-causing pathogens

| MIC in μg/mL | *Staph. aureus* | coa-neg *Staph.* | *Strep. agalactiae* | *Strep. dysgalactiae* | *Strep. uberis* | *Truep. pyogenes* |
|---|---|---|---|---|---|---|
| ≤0.063 | | | | | | 15 |
| 0.125 | 1 | | 12 | 11 | 2 | |
| 0.25 | 2 | 6 | 3 | 4 | 10 | |
| 0.5 | 12 | 6 | | | 3 | |
| 1 | | 2 | | | | |
| 2 | | | | | | |
| 4 | | | | | | |
| 8 | | 1 | | | | |
| 16 | | | | | | |
| 32 | | | | | | |
| 64 | | | | | | |
| >64 | | | | | | |
| Total tested | 15 | 15 | 15 | 15 | 15 | 15 |
| Minimum MIC | 0.125 | 0.25 | 0.125 | 0.125 | 0.125 | ≤0.063 |
| Maximum MIC | 0.5 | 8 | 0.25 | 0.25 | 0.5 | ≤0.063 |
| $MIC_{50}$ | 0.5 | 0.5 | 0.125 | 0.125 | 0.25 | ≤0.063 |
| $MIC_{90}$ | 0.5 | 1 | 0.25 | 0.25 | 0.5 | ≤0.063 |

MIC: minimum inhibitory concentration

In milk, the $MIC_{90}$ of avilamycin against *S. aureus* was significantly lower as the MIC 9 0 of penicillin G, an antibiotic indicated for the treatment of cow mastitis (Tab 3) 2.

The $MIC_{90}$ of evernimicin was identical to penicillin G.

TABLE 3

Distribution of MICs of avilamycin, evernimicin and penicillin G for *S. aureus* in milk

| | Distribution of MIC values for *S. aureus* (n = 20) | | | | | | | | | | | | |
|---|---|---|---|---|---|---|---|---|---|---|---|---|---|
| MIC (μg/ml) | ≤0.063 | 0.125 | 0.25 | 0.5 | 1 | 2 | 4 | 8 | 16 | 32 | 64 | >64 | $MIC_{90}$ |
| Avilamycin | 0 | 0 | 0 | 1 | 1 | 1 | 16 | 1 | 0 | 0 | 0 | 0 | 4 |
| Evernimicin | 0 | 0 | 0 | 0 | 0 | 0 | 4 | 11 | 5 | 0 | 0 | 0 | 16 |
| Penicillin G | 14 | 0 | 0 | 0 | 1 | 0 | 0 | 2 | 1 | 1 | 0 | 1 | 16 |

It has been surprisingly found that the polyether ionophore antimicrobials of International patent application WO2014/121343, such as salinomycin, lasalocid and monensin were active against different *S. aureus* isolates in bacteriological broth but showed no activity when investigated in milk as shown below in Table 4.

TABLE 4

*S. aureus* MICs of salinomycin, lasalocid and monensin in bacteriological broth and milk

| | Salinomycin | | Lasalocid | | Monensin | |
|---|---|---|---|---|---|---|
| Species | CAMHB | milk | CAMHB | milk | CAMHB | milk |
| *S. aureus* | 0.5 | >32 | 0.25 | >32 | 2 | >32 |
| *S. aureus* | 0.5 | >32 | 1 | >32 | 2 | >32 |
| *S. aureus* | 0.5 | >32 | 0.5 | >32 | 2 | >32 |
| *S. aureus* | 0.25 | >32 | 0.25 | >32 | 0.25 | >32 |
| *S. aureus* | 0.25 | >32 | 0.25 | >32 | 0.25 | >32 |
| *S. aureus* | 1 | >32 | 1 | >32 | 2 | >32 |
| *S. aureus* | 0.5 | >32 | 1 | >32 | 2 | >32 |
| *S. aureus* | 0.5 | >32 | 1 | >32 | 2 | >32 |

Example 2. Clinical Efficacy of Avilamycin in an Experimental Mastitis Infection Model The efficacy of avilamycin to treat mastitis in cows was demonstrated in an experimental infection model in lactating cows.

Methods

In short, the hind quarters of 10 healthy cows were infected with *Streptococcus uberis* by intramammary application of 100 bacteria per quarter. At appearance of clinical signs of the challenged quarters (abnormal milk appearance, swollen/hard quarter, pain on palpation) one hind quarter of each cow was treated with an oily suspension of avilamycin at a dose of 200 mg/quarter at three consecutive times after milking. Furthermore, the neighboring infected hint quarter showing clinical signs was mock treated with formulation vehicle at the identical dose volume and schedule. Milk samples were analyzed for *S. uberis* over a period of 21 days.

Result

The proportion of quarters free of *S. uberis* was substantially higher in quarters treated with avilamycin as compared to quarters treated with vehicle over the entire observation period (FIG. 1).

Example 3. Pharmacokinetic of Avilamycin after Intramammary Application

Systemic absorption of antibiotics after intramammary application leads to prolonged withdrawal times. Therefore, antimicrobials are favored which maintain high concentrations in the diseased udder in the absence of systemic distribution.

In order to assess the systemic exposure of avilamycin after intramammary treatment, avilamycin was applied intramammarily to one quarter each of 4 healthy cows at a dose of 200 mg/quarter in an oily suspension. Blood samples were taken prior to treatment (0 h) and at 1, 3 and 10 h after treatment. Plasma was generated and assessed for avilamycin using mass spectrometry.

As shown in Tab. 3, avilamycin was not detected at any time point in the plasma of treated cows.

TABLE 5

Plasma levels of avilamycin after intramammary application

| | time point (h) | | | |
|---|---|---|---|---|
| Animal ID | 0 | 1 | 3 | 10 |
| 506891 | <LOQ | <LOQ | <LOQ | <LOQ |
| 602082 | <LOQ | <LOQ | <LOQ | <LOQ |
| 102518 | <LOQ | <LOQ | <LOQ | <LOQ |
| 102420 | <LOQ | <LOQ | <LOQ | <LOQ |

LOQ: limit of quantification (50 ng/ml)

The invention claimed is:

1. A method for treating mastitis in an animal comprising administering to the animal an effective amount of an orthosomycin antimicrobial compound.

2. The method according to claim 1, wherein the orthosomycin antimicrobial compound is avilamycin.

3. The method according to claim 1, wherein the orthosomycin antimicrobial compound is evernimicin.

4. The method according to claim 1, wherein the orthosomycin antimicrobial compound is administered intramammarily.

5. The method according to claim 1, wherein the animal is a dry cow.

6. The method according to claim 1, wherein the animal is a lactating cow.

7. The method according to claim 1, wherein the mastitis is caused by *Staphylococcus* spp., *Streptococcus* spp, and/or Trueperella *pyogenes*.

8. The method according to claim 1 wherein a therapeutically effective amount of the orthosomycin antimicrobial compound is administered to the mammary gland of a cow.

9. The method according to claim 1 wherein the orthosomycin antimicrobial compound is administered to a cow with clinically manifest mastitis.

10. The method according to claim 9, wherein an additional non-antibiotic pharmacologically active component that is aimed at treatment of mastitis is administered to the animal in parallel.

11. The method according to claim 10, wherein an additional non-antibiotic pharmacologically active component is a specific or non-specific immunostimulant or a probiotic, a bacteriocin, a bacteriophage or a bacteriophage cocktail, phage endolysins or any other component that positively influences the body defense mechanism of the animal.

12. An intramammary injector comprising a pharmaceutical composition comprising a therapeutically effective amount of an orthosomycin antimicrobial compound and a pharmaceutically acceptable carrier.

13. The intramammary injector according to claim 12 comprising 25 to 1000 mg of the orthosomycin antimicrobial compound.

14. The intramammary injector according to claim 12, wherein the injector further comprises a teat seal formulation for forming a physical barrier in the teat canal of a dry cow.

15. The intramammary injector according to claim 12, wherein the orthosomycin antimicrobial compound is the sole antimicrobial compound.

* * * * *